United States Patent
Maloney et al.

(10) Patent No.: US 9,398,765 B2
(45) Date of Patent: Jul. 26, 2016

(54) APPARATUS AND METHOD FOR ELIMINATING ARTHROPOD INFESTATIONS

(75) Inventors: Paul Maloney, Dorval (CA); Tim Maloney, Dorval (CA); Laurel Maloney, Dorval (CA)

(73) Assignee: Eco Bug Doctor Inc., Quebec (CA)

( * ) Notice: Subject to any disclaimer, the term of this patent is extended or adjusted under 35 U.S.C. 154(b) by 258 days.

(21) Appl. No.: 13/993,494

(22) PCT Filed: Dec. 19, 2011

(86) PCT No.: PCT/CA2011/001395
§ 371 (c)(1),
(2), (4) Date: Jun. 12, 2013

(87) PCT Pub. No.: WO2012/083433
PCT Pub. Date: Jun. 28, 2012

(65) Prior Publication Data
US 2013/0263496 A1    Oct. 10, 2013

(30) Foreign Application Priority Data
Dec. 22, 2010 (CA) ..................... 2725936

(51) Int. Cl.
*A01M 1/10* (2006.01)
*A01M 3/00* (2006.01)
(Continued)

(52) U.S. Cl.
CPC .............. *A01M 3/007* (2013.01); *A01M 1/103* (2013.01); *A01M 1/14* (2013.01); *A01M 1/2094* (2013.01); *A61L 2/04* (2013.01); *A61L 2202/26* (2013.01)

(58) Field of Classification Search
USPC ................. 43/123, 132.1, 124, 109
See application file for complete search history.

(56) References Cited

U.S. PATENT DOCUMENTS

| 1,856,931 A | 5/1932 | Scott |
| 4,817,329 A * | 4/1989 | Forbes .............. 43/124 |

(Continued)

FOREIGN PATENT DOCUMENTS

| CA | 2387235 A1 * | 11/2002 |
| CA | 2752879 | 8/2010 |

(Continued)

OTHER PUBLICATIONS

Hall "Turn Up the Heat", *Pest Control* 57(2):66-67 (1989).

(Continued)

*Primary Examiner* — Christopher P Ellis
(74) *Attorney, Agent, or Firm* — Myers Bigel & Sibley (57) ABSTRACT

The present invention provides an encasement for preventing arthropods contamination of an object or for decontaminating an object contaminated with arthropods. The encasement comprises an enclosure defining an aperture, the enclosure being formed of an arthropod impervious material. The encasement also comprises a cover formed of an arthropod impervious material and shaped to cover the aperture, the cover being attachable to the enclosure to prevent arthropods from escaping or entering the encasement. The encasement also comprises a heating source linked to the encasement for heating an interior of the encasement and a heater control device connected to the heating source for controlling the temperature within the encasement. The aperture is sized to allow use of the object upon separation of the cover from the enclosure and the enclosure and cover are sized and shaped to completely house the object upon attachment between the cover and the enclosure.

19 Claims, 5 Drawing Sheets

(51) Int. Cl.
*A01M 1/20* (2006.01)
*A61L 2/04* (2006.01)
*A01M 1/14* (2006.01)

(56) References Cited

U.S. PATENT DOCUMENTS

| | | | | |
|---|---|---|---|---|
| 4,953,320 | A | * | 9/1990 | Nelson .......................... 43/121 |
| 4,961,283 | A | * | 10/1990 | Forbes .......................... 43/124 |
| 5,569,401 | A | * | 10/1996 | Gilliland et al. ............. 219/386 |
| 6,141,901 | A | * | 11/2000 | Johnson et al. ................ 43/124 |
| 6,279,261 | B1 | * | 8/2001 | Binker et al. .................. 43/125 |
| 6,588,140 | B1 | * | 7/2003 | Johnson et al. ................ 43/124 |
| 6,772,829 | B2 | * | 8/2004 | Lebrun ........................ 165/121 |
| 7,690,148 | B2 | * | 4/2010 | Hedman ...................... 43/132.1 |
| 8,742,296 | B2 | * | 6/2014 | Bermudez .................... 219/385 |
| 2005/0246942 | A1 | * | 11/2005 | Mueller et al. ................ 43/124 |
| 2009/0211148 | A1 | | 8/2009 | McCarty |
| 2010/0043275 | A1 | | 2/2010 | Battick |
| 2011/0064605 | A1 | * | 3/2011 | Hedman .......................... 422/3 |
| 2012/0186138 | A1 | * | 7/2012 | Bell et al. ....................... 43/125 |
| 2012/0216444 | A1 | * | 8/2012 | Raud et al. ................... 43/132.1 |
| 2013/0263496 | A1 | * | 10/2013 | Maloney et al. ............... 43/114 |
| 2013/0269239 | A1 | * | 10/2013 | Whitley et al. .............. 43/132.1 |
| 2014/0013653 | A1 | * | 1/2014 | Lander ........................ 43/132.1 |

FOREIGN PATENT DOCUMENTS

| | | |
|---|---|---|
| FR | 2867411 | 9/2005 |
| GB | 379439 | 9/1932 |
| GB | 490008 | 8/1938 |
| GB | 2283174 | 5/1995 |
| JP | 2156984 | 6/1990 |

OTHER PUBLICATIONS

Pipkin, Sr. "Transmission of *Trypanosoma cruzi* by Arthropod Vectors: Anterior versus Posterior Route Infection", *Int. Rev. Trop. Med.* 3:1-47 (1969).

Blow, J.A. et al., 2001 Stercorarial shedding and transtadial transmission of hepatitis B virus by common bed bugs (Hemiptera: Cimicidae). J. Med. Entomol. 38(5): 694-700.

Ogston, C.W. et al., Persistence of hepatitis B surface antigen in the bedbug *Cimex hemipterus* (Fabr.). J Infect Dis. Sep. 1979; 140 (3): 411-414.

Mallis, A. 1990, Handbook of Pest Control: The behavior, Life History and Control of Household Pests. Seventh Edition, Franmk & Foster Co, Cleveland, Ohio, p. 980.

Olkowski, W. et al., 1991, Common Sense Pest Control, Taunton, Newton, CT.

Kells, S.A. 2006, Nonchemical control of Bed Bugs, American Entomologist, 52(2):109-110.

Montreal Insectarium, 2008, Punaise des lits, La toile des insectes du Québec, URL: www.ville.montreal.qc.ca/insectarium.

Gangloff-Kaufmann, J..C 2006, Bed bugs in America: a pest management industry survey. Am. Entomol. 52(2): 105-106.

Romero, A. et al., 2007, Insecticide resistance in the bed bug: a factor in the pest's sudden resurgence? J. Med. Ent. vol. 44, No. 2, pp. 175-178.

Alavanja, M.C.R. et al., 2003, Use of agricultural pesticides and prostate cancer risk in the Agricultural Health Study Cohort. Am. J. Epidemiol. 157(9):800-814.

Kaneko, H., Miyamoto, J., 2001, Pyrethroid chemistry and metabolism. Chapter 58 Handbook of Pesticide Toxicology, vol. 2: Agents (Krieger R, Doull J, Ecobichon D, eds). San Diego: Academic Press, 1263-1288.

Narahashi, T., 2001, Neurophysiological effects of insecticides. Chapter 12 Handbook of Pesticide Toxicology, vol. 1: Principles (Krieger R, Doull J, Ecobichon D, eds). San Diego: Academic Press, 335-351.

Soderlund, D.M. et al., 2002 Mechanisms of pyrethroid neurotoxicity: implications for cumulative risk assessment. Toxicology 171:3-59.

Harlan, K.J., 2006, Bed bugs 101: the basics of Cimex lectularius. Am. Entomol. 52(2): 99-101.

Written Opinion of the International Searching Authority corresponding to International Application No. PCT/CA2011/001395 mailed Mar. 20, 2012.

Notification of Transmittal of the International Preliminary Report on Patentability corresponding to International Application No. PCT/CA2011/001395 mailed Mar. 11, 2013.

International Search Report corresponding to International Application No. PCT/CA2011/001395 mailed Mar. 20, 2012.

* cited by examiner

APPARATUS AND METHOD FOR ELIMINATING ARTHROPOD INFESTATIONS

RELATED APPLICATIONS

This application is a 35 U.S.C. §371 national stage application of PCT Application No. PCT/CA2011/001395, filed on Dec. 19, 2011, which claims priority from Candian Application No. 2,725,936 filed on Dec. 22, 2010. The contents of each of these applications are incorporated herein by reference in their entireties. The above-referenced PCT International Application was published as International Publication No. WO 2012/083433 A1 on Jun. 28, 2012.

FIELD OF THE INVENTION

The present invention relates generally to an apparatus and method for preventing arthropods contamination of an object or for decontaminating an object contaminated with arthropods. More particularly the invention relates to an encasement which eliminates arthropods and which allows a contaminated object to be used normally upon opening of the encasement.

BACKGROUND

Arthropods such as bed bugs had been a common part of life before the use of chlorinated hydrocarbons and other synthetic insecticides became widespread in the 1940s and 1950s. Though never completely eradicated, their presence was minimal until their recent resurgence some 10 years ago. Their resurgence has been a devastating and expensive event in the lives of many people today. Bed bugs cause loss of sleep, stress, social alienation, as well as physical distress. In rental property and the hospitality industry among many others, litigation is prevalent. Throughout the world, large cities are being overwhelmed by bed bug proliferation. People are needlessly exposed to pesticides, and are experiencing loss of belongings, and financial distress as they deal with an infestation. There is also a possibility of disease transmission, as studies show hepatitis B and, in endemic areas, American trypanosomiasis (Chagas disease) may be mechanically transmitted by bed bugs (Blow J A et al. 2001 Stercorarial shedding and transtadial transmission of hepatitis B virus by common bed bugs (Hemiptera: *Cimicidae*). *J. Med. Entomol.* 38:694-700, Ogston C W, et al. Persistence of hepatitis B surface antigen in the bedbug Cimex hemipterus (Fabr.). *J Infect Dis*. September 1979; 140 (3):411-4 and Pipkin AC Sr. Transmission of *Trypanosoma cruzi* by arthropod vectors: anterior versus posterior route infection. *Int Rev Trop Med.* 1969; 3:1-47.

There are a number of techniques used to reduce or eliminate bed bugs. The most common is the use of insecticides. The elusive and stealthy nature of bed bugs allows them to escape treatments all too frequently. Isolation of humans is attempted with numerous devices and methods including zippered bed bug-proof mattress covers, bed-leg moat devices, and other barriers. Killing and eradication of bed bugs is attempted with insecticide application, vacuuming, and a host of techniques for heat treating or freezing the insects: cryogenic freezing equipment, heat treatment setups, and steam treatment.

Heat Treatment

This method of bed bug control involves raising temperatures to or above the killing temperature for bed bugs. In this case, a killing temperature is a temperature known to kill bed bugs in a given length of time. Some of the drawbacks for heat treatments include the amount of time required to bring core temperatures (interior temperature of materials) high enough to effectively kill bed bugs that may have taken refuge within materials. This contributes to the heat treatments generally being expensive procedures. The setup in order to effectively heat treat materials in the room, as well as insertion of heating ducting into the building through windows can be intrusive and cause embarrassment to the person affected.

Finally, following a heat-treatment, a room may be easily re-infested, as bed bugs are able to retreat into cracks and crevasses in walls, ceilings and floors, where they may escape treatment. Consequently there is a need to overcome these problems by providing an easy and relatively unobtrusive way to repeatedly heat-treat bed bug infested materials within the area they most often inhabit: the bed/couch environment.

Most insects cannot survive temperatures above 49° C. for over 30 minutes (Hall R. 1989. Turn up the heat. *Pest Control.* 57(2):66, 67 as quoted in Mallis A. 1990. Handbook of Pest Control: The Behavior, Life History and Control of Household Pests. Seventh Edition. Franmk & Foster Co, Cleveland, Ohio. p. 980). The minimum killing temperature for bed bugs is thought to be 44-45° C. (Olkowski W. et al. 1991 *Common Sense Pest Control*. Taunton, Newton, Conn.). The killing duration, which is the length of time required to kill bed bugs at a given killing temperature, is debated. Kells suggests that a 45° C. core exposure for 2 hours, should be the minimum target temperature for heat treatments (Kells S. A. 2006. Nonchemical control of Bed Bugs. *American Entomologist.* 52:2: p. 110). Another source suggests that temperatures above 46° C. can kill all stages of the bed bug in less than 10 minutes (Montreal Insectarium. 2008. Punaise des lits. La toile des insectes du Québec. URL: www.ville.montreal.qc.ca/insectarium). A "complete treatment" is when heat has penetrated the contents of a heating chamber such that the contents have at least reached a killing temperature for at least the appropriate killing duration.

Pesticides

The pesticide approach often requires multiple visits and may not always be effective due to pesticide resistance and dispersal of the bed bugs. According to a 2005 survey, only 6.1% of companies claim to be able to eliminate bed bugs in a single visit, while 62.6% claim to be able to control a problem in 2-3 visits (Gangloff-Kaufmann J. C. et al. 2006 Bed bugs in America: a pest management industry survey. *Am. Entomol.* 52: 105-106). Insecticide application may cause dispersal of bed bugs to neighboring areas of a structure, spreading the infestation. Furthermore, the problem of insecticide resistance in bed bug populations increases their opportunity to spread. Studies of bed bug populations across the United States indicate that resistance to pyrethroid insecticides, which are used in the majority of bed bugs cases (Gangloff-Kaufmann J. C. et al. 2006 Bed bugs in America: a pest management industry survey. *Am. Entomol.* 52: 105-106) is widespread (Romero A. et al. 2007. Insecticide resistance in the bed bug: a factor in the pest's sudden resurgence? *J. Med. Ent. Vol.* 44, No. 2, pp. 175-178). Treatment failures are prevalent and repeated services are financially devastating to many people. Consequently there is a need to provide an apparatus that effectively lures and kills bed bugs before they can further reproduce. In addition, this prevents spreading of bed bugs by the discarding of contaminated belongings, which are often picked up by others.

Non-residue methods of mattress treatment are desired, in place of contaminating mattresses with insecticides. Spraying the mattress with insecticide is undesirable as the room must be suitably ventilated, sufficient time must be given after application before the mattress can be used again and there is a risk of the user having an allergic reaction to the chemicals, not to mention other possible health risks including cancer (Alavanja MCR et al. 2003 Use of agricultural pesticides and prostate cancer risk in the Agricultural Health Study Cohort. *Am. J. Epidemiol.* 157:1-13) and acute neurotoxicity (Kaneko H, Miyamoto J. 2001 Pyrethroid chemistry and metabolism. In: Handbook of Pesticide Toxicology, Vol 2: Agents (Krieger R, Doull J, Ecobichon D, eds). San Diego:Academic Press, 1263-1288, Narahashi T. 2001 Neurophysiological effects of insecticides. In: Handbook of Pesticide Toxicology. Vol 1: Principles (Krieger R, Doull J, Ecobichon D, eds). San Diego: Academic Press, 335-350 and Soderlund D M et al. Mechanisms of pyrethroid neurotoxicity: implications for cumulative risk assessment. *Toxicology* 2002; 171:3-59). Concerns over the possible effects of pesticides on the health of people and pets, as well as the dispersal of bed bugs to neighboring dwellings due to repellant effects of insecticides, make the practice of chemically treating the mattresses problematic.

Bed bugs can disperse throughout a building in many ways. The moving of potentially infested materials can spread the problem within a home environment. Bed bugs are also commonly spread to other rooms when occupants abandon their normal place of sleep, and the bed bugs disperse to seek out a host. They may also spread in reaction to application of insecticides. Typically, if the host remains in situ, the bed bugs will not travel far beyond the bed. According to a survey, the most commonly infested places are the mattress (98.2%), boxspring (93.6%), as well as nearby carpets and baseboards (94.1%) (Gangloff-Kaufmann, J. C. et al. 2006 Bed bugs in America: a pest management industry survey. *Am. Entomol.* 52: 105-106). In fact, bed bugs thrive in areas where there is an adequate supply of available hosts, and plenty of cracks and harborages within 1.5 m of the host (Harlan H. J. 2006 Bed bugs 101: the basics of *Cimex lectularius*. *Am. Entomol.* 52: 99-101).

Thus there is presently a need to provide a system that allows the person to remain in their normal place of sleep, thus attracting the bed bugs to the bed/couch area, and discouraging their dispersal. Yet the person may sleep undisturbed, as they are protected from being bitten by the collection devices on the legs of the bed.

Because of the treatment drawbacks of the various means of bed bug control, people are less likely to take action frequently enough to mitigate the problem and consequently the bed bugs have time to lay eggs and reproduce quickly. Treatments can be costly, laborious, time consuming, boring, repetitive, may entail health risks, and cause embarrassment to the person affected. For example, steam-cleaning, which is effective at killing bed bugs, requires repeated and very thorough steaming of the mattress, boxspring, bed frame, bed covers, pillows, not to mention other materials and objects within the infested room, such as carpets and curtains. Rooms are also often cluttered, providing many harborages and passages for bed bugs. This can make treatment of a room awkward, tedious and easily inadequate. Consequently there is a need for a system that allows for an easy and non-time-consuming way to treat the bed/couch and other materials, taking a bite out of the bed bug population, and providing the user with peace of mind and a safe resting/sleeping environment.

SUMMARY OF THE INVENTION

An object of the present invention is to address at least one of the above-mentioned needs.

In accordance with a first aspect of the invention, there is provided an encasement for preventing arthropods contamination of a furniture element or for decontaminating a furniture element contaminated with arthropods, the encasement comprising an enclosure defining an aperture, the enclosure being formed of an arthropod impervious material and the enclosure is configured to partially house the furniture element. The encasement also comprises a cover formed of an arthropod impervious material and shaped to cover the aperture to prevent arthropods from escaping or entering the encasement, the cover being attachable to the enclosure and the cover being configurable between an opened position and a closed position. The encasement also comprises a heating source linked to the encasement for heating an interior of the encasement and a heater control device connected to the heating source for controlling the temperature within the encasement. In the opened position, the aperture is sized to allow unobstructed use of the furniture element while at least part of the furniture element remains within the enclosure and in the closed position, the enclosure and cover are sized and shaped to completely house the furniture element.

In accordance with a second aspect of the invention, there is provided a method for preventing arthropods contamination of a furniture element or for decontaminating a furniture element contaminated with arthropods, the method comprising the steps of: a) providing an encasement having: an enclosure defining an aperture, the enclosure being formed of an arthropod impervious material and the enclosure is configured to partially house the furniture element; a cover formed of an arthropod impervious material and shaped to cover the aperture to prevent arthropods from escaping or entering the encasement, the cover being attachable to the enclosure and the cover being configurable between an opened position and a closed position; a heating source linked to the encasement for heating an interior of the encasement; and a heater control device connected to the heating source for controlling the temperature within the encasement, wherein in the opened position, the aperture is sized to allow unobstructed use of the furniture element while at least part of the furniture element remains within the enclosure and wherein in the closed position, the enclosure and the cover are sized and shaped to completely house the furniture element; b) disposing the furniture element within the encasement; c) attaching the cover to the enclosure; and d) activating the heater control device for heating the interior of the encasement for a fixed period of time.

BRIEF DESCRIPTION OF THE DRAWINGS

These and other objects and advantages of the invention will become apparent upon reading the detailed description and upon referring to the drawings in which.

DETAILED DESCRIPTION OF PREFERRED EMBODIMENTS OF THE INVENTION

The present invention relates to a heating encasement and a method for preventing arthropod contamination of an object or for alleviating arthropod infestation within an object, allowing the object to be used normally upon opening the encasement. The contaminated object of the present invention is defined as any object where people sleep or rest for a prolonged period of time, and that may harbour arthropods such as bed, couch, futon, seat, chair, mattress, box spring, bed frame, In one embodiment, the object is inflatable and in another embodiment, the object is foldable. This object is the place where people are most often bitten or experience allergic reactions to arthropod derived materials. Since bed bugs feed only on blood, they hide in seams and crevasses in and around the object which gives them access to a reliable food source. Other examples of arthropods are dust mites, clothes moths, dermestids, triatomide bugs, sac spiders and the like.

Figure 1:
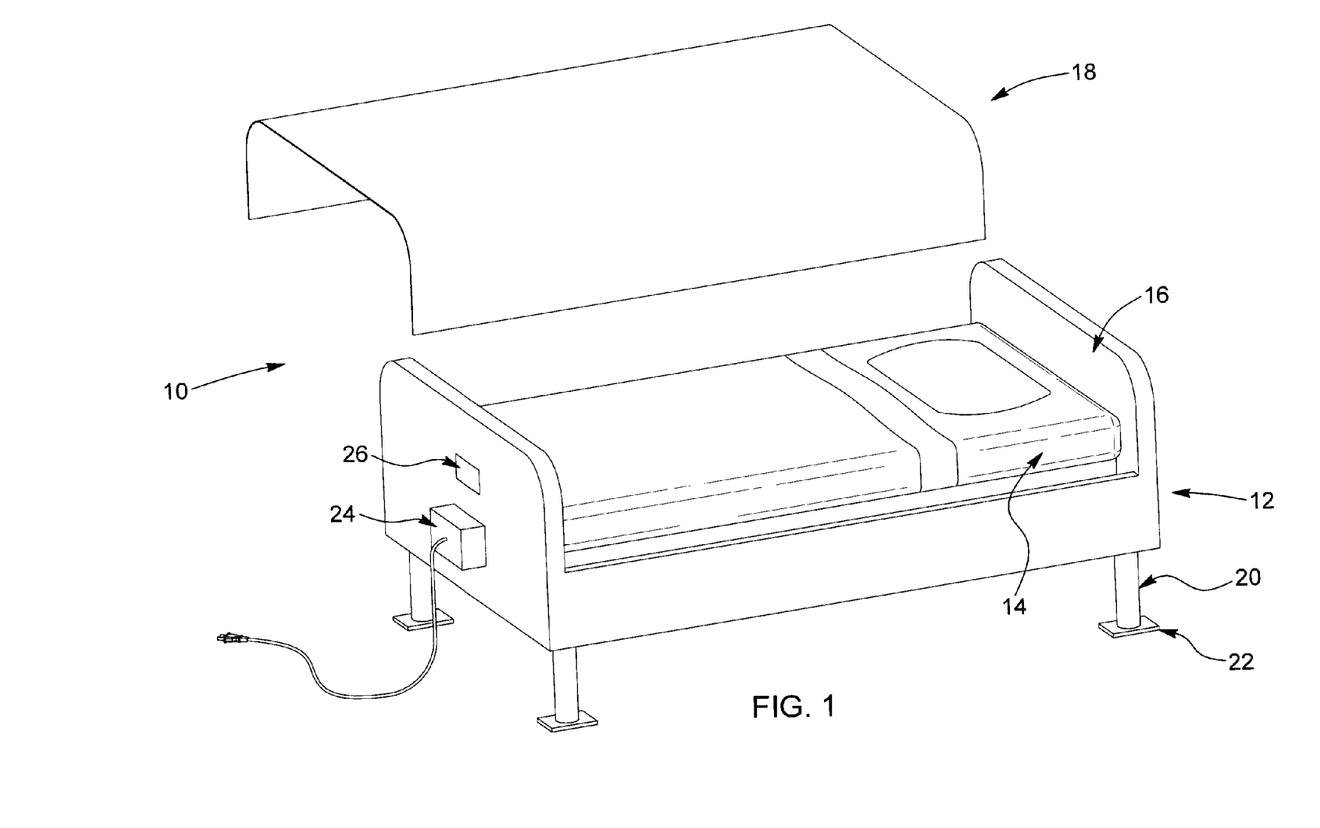
FIG. 1 is a perspective side view of the encasement according to a preferred embodiment of the present invention shaped to receive a mattress, with the cover removed from the enclosure.
Figure 2:
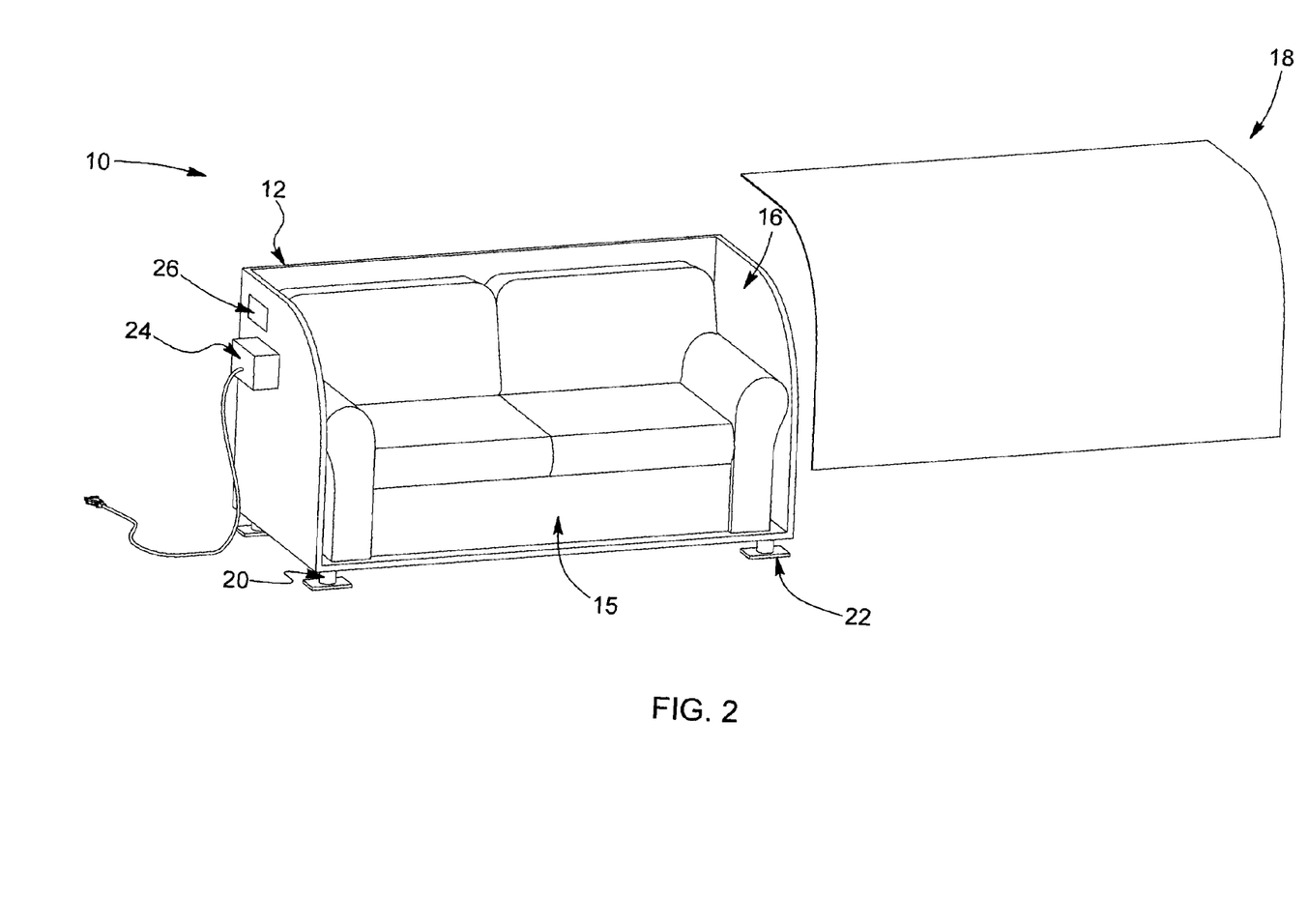
FIG. 2 is a perspective front view of the encasement, according to another preferred embodiment of the present invention, shaped to receive a couch with the cover removed from the enclosure.
Figure 3:
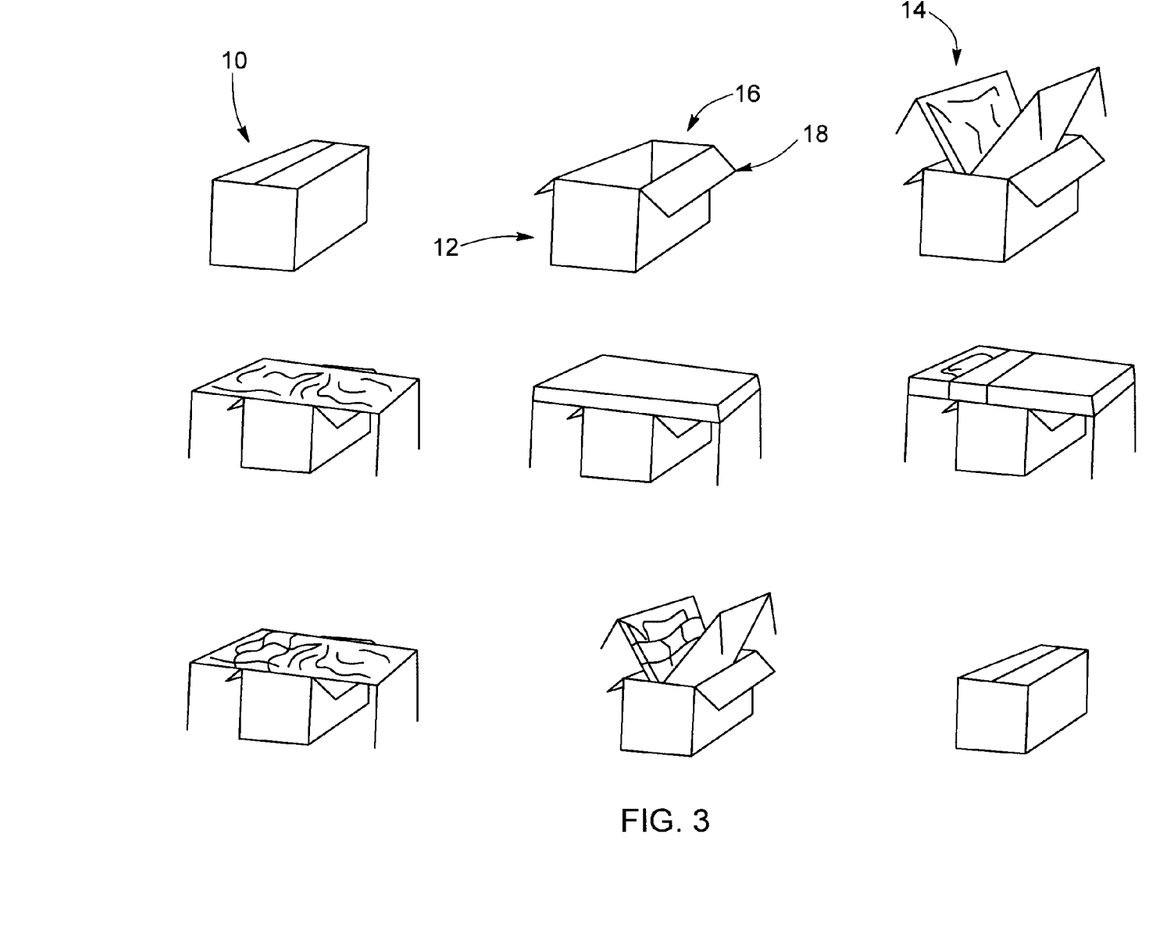
FIG. 3 is a sequence diagram of a foldable bed collapsible in and out of the encasement of the present invention, according to another preferred embodiment of the present invention.
Figure 4:
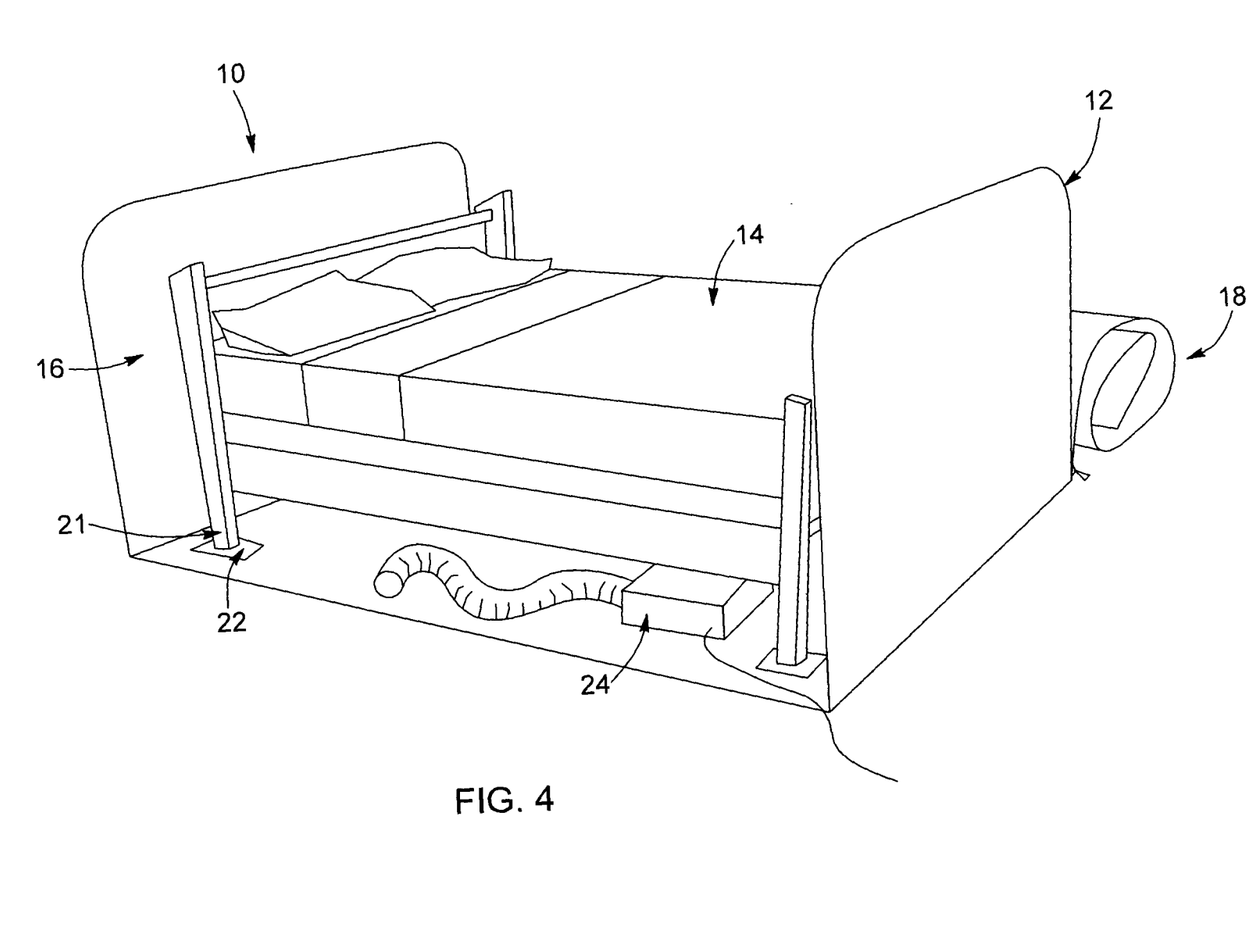
FIG. 4 is a perspective side view of the encasement according to another preferred embodiment of the present invention shaped to receive a bed including frame, with the cover removed from the enclosure.
Figure 5:
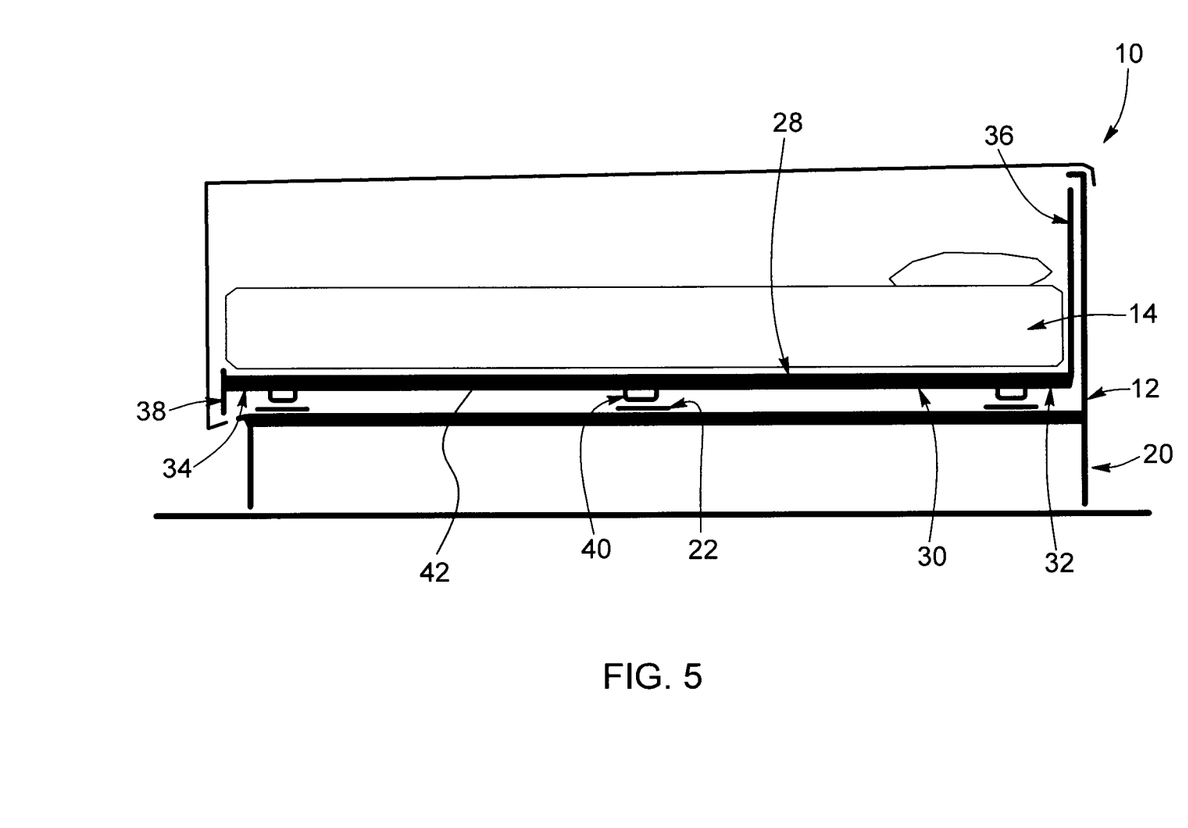
FIG. 5 is a side view of the encasement according to another preferred embodiment of the present invention shaped to receive a mattress.

Referring to FIGS. 1 2 4 and 5, there is shown an encasement 10 according to the present invention. The encasement comprises an enclosure 12 formed of an impervious material impenetrable to arthropods. The interior of the enclosure 12 is a heating chamber. The enclosure 12 is sized to contain a given object 14 such as bed (home, hospital, hotel, hostel), couch 15, bunk bed, bed frame, cot, futon, mattress (and box springs), chair, air plane seat and theatre seat. In one embodiment, the enclosure 12 is designed to completely encase a mattress and possibly a box spring as shown in FIGS. 1 and 5, a bed frame as shown in FIG. 4 including or not a mattress and/or a box spring or a couch 15 as shown in FIG. 2. In another embodiment, the object 14 is an inflatable object which can be configured between a retracted and an expanded configuration. In the retracted configuration, the object is completely housed within the encasement for decontamination. In the expanded configuration, the object can be used and can expand partially outside the enclosure 12. FIG. 3 shows another embodiment, in which the object 14 is inside the encasement 10 for decontamination and outside the encasement 10 for use.

In one embodiment, the exterior enclosure surface is smooth and without crevices or passages being free of arthropod harbourages. In another embodiment, the enclosure 12 is insulated such as with Styrofoam to prevent heat loss and increase the efficiency of the heating chamber.

The enclosure 12 further defines an aperture 16 allowing use of the object 14. As shown in FIGS. 1, 2, 4 and 5, the aperture 16 is sized to allow normal use of the object 14 upon providing the object within the enclosure 12. In another embodiment, as shown in FIG. 3, the aperture 16 allows the object 14 to be unfolded outside of the encasement 10 allowing use of the object 14. As such, the aperture 16 allows use of the object when it is not being decontaminated.

The encasement 10 also comprises a cover 18 formed of an arthropod impervious material and shaped to cover the aperture 16. The cover 18 is attachable to the enclosure 12 and prevents arthropods from escaping or entering the encasement. The cover 18 is attachable to the enclosure 12 by known means such as zipper, Velcro™, magnet, buttons etc. In another embodiment, the cover 18 is sealably attachable to the enclosure 12 to prevent both heat loss and arthropod passage. When the cover 18 is attached to the enclosure 12, the object 14 is completely housed within the enclosure for decontamination as shown in FIGS. 1 to 5. The cover 18 when opened or separated from the enclosure 12 allows for use of the object and allows also loading or unloading of objects into and out of the enclosure 12. The cover 18 is designed such that when opened or separated from the enclosure 12, it provides enough access so as to allow for normal, everyday use of the object 14 contained therein. For example, a bed in the enclosure 12 would have access from at least one side as shown in FIGS. 1, 4 and 5, or a couch in the enclosure 12 could be sat in normally without obstruction, as shown in FIG. 2. In one embodiment, upon opening the cover 18, the enclosure 12 contains a bed therein and a cover 18 that lifts to form a canopy over the bed, giving normal access to the bed contained therein. In another embodiment, upon opening the cover 18, the object deploys outside of the encasement 10 allowing normal use of the object as shown in FIG. 3. In another embodiment, the cover 18 is composed of a flexible insulating material, allowing for the cover 18 to be folded or rolled to a smaller size as shown in FIG. 4. In one embodiment, the cover 18 can be placed under the enclosure.

In one embodiment, the encasement 10 is sized to provide space for loading additional objects therein for treatment in addition to the object 14 such as pillow, blanket, sheet, duvet, bag, carpet, linen, clothing, curtain electronics or books. The extra loading space is preferably on the top surface of object 14. Optionally, the encasement 10 can be expanded (with insulated panels for example) to enclose other larger objects therein for treatment in addition to the object 14.

In one embodiment, the enclosure 12 is elevated off the floor as shown in FIGS. 1, 2 and 5 preferably by at least one inch by at least one leg 20 to prevent crawling arthropods in the surrounding environment from reaching the exterior of the encasement 10.

In another embodiment, the encasement 10 is protected from re-infestation by arthropods by trap 22 such as glue trap located at the base of the leg 20 of the enclosure 12 as shown in FIGS. 1 and 2. In another embodiment, object 14 is isolated from crawling arthropods with traps within the aperture 16. In this embodiment, the trap 22 is positioned between the object 14 and the encasement 10 such as at the base of the leg 21 of the bed frame as shown in FIG. 4 or leg 40 as shown in FIG. 5. As a result, the user of the object 14 acts as bait for trapping arthropods located in the surrounding infested area. In a preferred embodiment, trap 22 is a glue trap. The presence of leg 20 and trap 22 may not be necessary in some designs of the encasement.

The encasement 10 also contains a heating source 24 to heat the interior of the encasement 10. In one embodiment, the heat source 24 utilizes a standard 120V AC electrical outlet for convenience. In another embodiment, the encasement 10 comprises a heat circulating system (not shown). Heat is distributed throughout the encasement 10 to elevate the temperature inside the encasement 10 and its content. In another embodiment, heat is distributed with priority to the seams of the cover 18, and towards an interface between the enclosure 12 and the cover 18 and any other possible arthropod escape routes of the enclosure 12, making escape of live arthropods from the encasement 10 improbable during treatment. Different types of heat source 24 are suitable for use with the encasement 10.

In one embodiment, heat source 24 is an electrical air heater such a space heater or heat gun. The hot air is re-circulated throughout the encasement 10 so as to reduce heat loss or arthropods escape. Air movement can be facilitated by means of small fans distributed within the air space of the encasement 10. In this embodiment, air circulation is needed on all sides of the object 14 and other objects being treated to allow for proper heat penetration. This is accomplished, for example, if the object 14 is supported from below within the enclosure 12 by a rack or grill. The rack would create an air space below to allow for air passage. Alternately, the object 14 is supported by a thermally conductive structure such as aluminum with an array of air passages through it. The heat could therefore be conducted to the underside of the object 14 as hot air passes through the air passages. In either case, ducts or heat sinks may focus heat to the seams of the cover 18 and to the interface between the enclosure 12 and the cover 18 to prevent escape of arthropods during treatment. Optionally, heat could be focused to known arthropod harbourages within the enclosure 12 in a similar manner.

In another embodiment, heat source 24 comprises electrically heated surfaces such as heating tape or heating mesh. In this embodiment, the electrically heated surfaces are distributed on the internal surfaces of the encasement 10. This heating source is by nature already distributed and does not require an air space or air circulation. Optionally, additional layers of heating mesh are implemented such as between a box spring and mattress, between a couch and its cushions or between the object 14 and additional object being treated. This allows for heat to penetrate the contents of the encasement 10 at a much faster rate. In another embodiment, the electrically heated surfaces are strategically positioned within the encasement 10, such as along the seams of the cover 18, at the interface between the enclosure 12 and the cover 18 or in known arthropod harbourages. In another embodiment, different sections of electrically heated surfaces are heated alternately at a set frequency to prevent over heating of any given section and facilitate the penetration of heat into the content of encasement 10.

In another embodiment, heat source 24 is an electrical water heater comprising a hot water tank. The advantage of this heat source is that the water temperature within the reservoir tank can be brought up before treatment which allows for quick responsive heat. During treatment, the hot water would be pumped through a closed loop array of tubing distributed on the interior walls of the encasement 10. This array may run through heat sinks such as aluminum plates which conduct the heat to the encasement 10 contents. Like with electrically heated surfaces, an air space and air circulation is not required for heat distribution within the encasement 10. Optionally, the tubing array and heat sinks focus heat along the seams of the cover 18, at the interface between the enclosure 12 and the cover 18 or in known arthropod harbourages.

The encasement 10 also comprises a heater control device 26 connected to the heating source 24 allowing control of the temperature within the encasement 10 as well as the treatment duration. In one embodiment, the heater control device 26 runs a program for treating automatically at a set frequency (preset treatment schedule). The first component of the heater control device 26 is a thermostat designed to keep the encasement 10 from reaching dangerous temperatures. This thermostat would bypass all other controls, shutting off the heating source 24 once temperatures within the encasement 10 reach a designated cut off maximum around 60-70° C. The main function of the heater control device 26 is to ensure a complete treatment by reaching the arthropods killing temperature for at least an appropriate killing duration. A complete treatment can be accomplished in several ways.

In one embodiment, complete treatment is accomplished with a temperature probe set in contact with the object 14 to track when the interior of the object 14 has reached the intended killing temperature. Once the killing temperature is reached, a timer is set off to end the treatment cycle after the appropriate duration at that killing temperature. In another embodiment, complete treatment is accomplished with a timer for a predetermined length of time known to be ample for appropriate penetration of heat into the interior of the encasement 10. Though much simpler in design, the second embodiment does not allow for the object 14 to adapt its treatment cycle to materials that heat at different rates.

In one embodiment, the encasement 10 comprises safety features. A cover engagement switch could prevent the operation of a treatment cycle unless the encasement 10 is properly closed. The cover should not lock shut such that it can be opened from the inside. In another embodiment, an indicator light indicates when a treatment is in progress, and another indicator light indicates when a successful treatment has been completed.

Referring to FIG. 5, there is shown an encasement 10 according to another embodiment of the present invention. The encasement 10 further comprises an isolating structure 28 for isolating the object 14 to be decontaminated with respect to the enclosure 12. The isolating structure 28 spatially offsets the object 14 to be decontaminated with respect to the enclosure 12 thus preventing the arthropods from reaching the object 14. The isolating structure 28 further comprises at least one supporting leg 40. This isolation of the object 14 effectively provides a better decontamination environment as it: 1) allows better air circulation 2) prevents object 14 from making contact with non-isolated or non-decontaminated surfaces, and 3) in conjunction with traps, lures and traps arthropods in the surrounding environment after decontamination, thus preventing the recontamination of object 14 and protecting the user of object 14.

In one embodiment, the isolating structure 28 comprises a first surface 30 having a first end 32, a second end 34 opposing the first end 32, and a pair of lateral edges 42 extending from the first end 32 to the second end 34. An overhang structure 38 is provided along the pair of lateral edges 42 and the second end 34. The overhang structure 38 can overhang the leg 20 of the enclosure. When the encasement is used for bedding application, the overhang structure 38 prevents bedding hanging over the edge from contacting non-isolated and non-decontaminated structures as shown in FIG. 5. The isolating structure 28 further comprises a second surface 36 extending upwardly from the first end 32. The second surface 36 and the overhang structure 38 being offset with the enclosure 12 prevent the object 14 from contacting the enclosure 12 after decontamination. In a preferred embodiment, for bedding application, the second surface 36 is a headboard preventing contact of pillows and bedding with non-isolated and non-decontaminated structures.

In one embodiment, a trap is placed between the isolating structure 28 and the enclosure 12. In one embodiment, a glue trap 22 is provided between the leg 40 and the enclosure 12.

Another object of the present invention is to provide a method for preventing arthropods contamination of an object or for decontaminating an object contaminated with arthropods with an encasement as described above. Encasement 10 is implemented in environments with known or suspected arthropod infestations. Encasement 10 is also used as a preventative measure against arthropods, especially in places prone to infestations such as hotels, hostels and lounges. Encasement 10 is provided for each objects suspected of being infested within an infested environment. The object 14 is disposed within the enclosure 12 and can be used upon separation of the cover 18 from the enclosure 12. The user should avoid resting in other non encased objects avoiding the migration of arthropods to a new location. In one embodiment, the encasement 10 and the object 14 contained therein are intended to be positioned more or less how the object 14 was prior to be disposed within the encasement 10. In another embodiment, the encasement 10 does not touch any walls, floors or objects to avoid crawling arthropods from entering into the encasement 10. Optionally glue trap 22 is provided under the leg 20 of the encasement 10.

To start a treatment cycle, the user closes the cover 18 and then activates the heater control device 26 such as by pressing a button, or turning a timer which then causes the treatment cycle to begin. The encasement 10 shuts off once a treatment cycle is complete, at which point the cover 18 may be opened. After a treatment cycle, the object 14 is used normally if desired.

The treatment schedule is adjusted as needed. An advantage of the encasement 10 of the present invention is its ability to respond quickly and repeatedly to an infestation. The temperature within the encasement 10 is maintained between 44-70° C. between 30 minutes to 6 hours to kill all stages of arthropods. In a heavy infestation, a daily treatment is desired. For light infestations, a weekly treatment is more convenient. In a hotel, a treatment between uses is appropriate. Optionally, treatments are done immediately after noticing bites or noticing signs of arthropods such as live specimens, eggs, markings on the object, etc. Treatments are repeated until the infestation is overcome. In one embodiment, a treatment of at least once a week is done for at least 2 weeks after arthropods are suspected to have been eliminated. Extra treatments should be done for at least the length of the gestation period of arthropods in the given environment. During the course of the infestation, the user should always use the object disposed within the encasement 10. The object disposed within the encasement 10 also acts as a sanctuary for the victims of arthropod infestations. At the same time, encasement 10 prevents further arthropods dispersal, and acts as bait to trap the arthropods in the glue trap 22. In one embodiment, the glue trap is checked on a weekly basis and replaced when the glue seems no longer sticky or when too much debris is caught in the trap.

The encasement of the present invention has the following advantages:

It provides an object encasement for alleviating arthropod infestations within the object which can be used normally.

It provides an object encasement for preventing arthropods contamination of an object or for alleviating arthropod infestations which can be left in place around the object between treatments and when the object is in use.

It provides a method for preventing arthropods contamination of an object or for alleviating arthropod infestations within and around an object.

It provides an object encasement for preventing arthropods contamination of an object or for alleviating arthropod infestations which can be implemented quickly and repeatedly with minimal work on the part of the user.

It provides an object free of arthropods so the user can be relieved of arthropod biting even before the infestation is eliminated.

It displaces the use of chemical pesticides and all the disadvantages associated with chemical pesticides such as health risks, arthropod repulsion and spread, inconvenience, etc.

The traps capture and kill arthropods attracted to the user of the object, thus depleting the arthropod population in the surrounding infested environment.

It provides the ability to treat additional objects within the enclosure, with or without expanding the enclosure.

It prevents the unnecessary and costly disposal and replacement of infested objects.

It prevents the further spread of arthropods through disposal/moving of infested objects.

It attracts arthropods and traps them, thus discouraging dispersal.

While embodiments of this invention have been illustrated in the accompanying drawings and described above, it will be evident to those skilled in the art that changes and modifications may be made therein without departing from the essence of this invention.

What is claimed:

1. An encasement for preventing arthropods contamination of a furniture element or for decontaminating a furniture element contaminated with arthropods, the encasement comprising:
   an enclosure defining an aperture, the enclosure being formed of an arthropod impervious material and the enclosure is configured to partially house the furniture element;
   a cover formed of an arthropod impervious material and shaped to cover the aperture to prevent arthropods from escaping or entering the encasement, the cover being attachable to the enclosure and the cover being configurable between an opened position and a closed position;
   a heating source linked to the encasement for heating an interior of the encasement; and
   a heater control device connected to the heating source for controlling the temperature within the encasement,
   wherein the furniture element is a sittable furniture element selected from the group consisting of beds, futons, couches, seats, chairs, mattresses, box springs, and bed frames, wherein, in the opened position, the aperture is sized to allow unobstructed sitting on the sittable furniture element while at least part of the furniture element remains within the enclosure and wherein in the closed position, the enclosure and the cover are sized and shaped to completely house the furniture element.

2. The encasement of claim 1, wherein the arthropods are bed bugs, dust mites, clothe moths, dermestids, triatomide bugs or sac spiders.

3. The encasement of claim 2, wherein the enclosure further comprises smooth exterior surfaces.

4. The encasement of claim 3, wherein the cover is sealably attachable to the enclosure.

5. The encasement of claim 4, further comprising a heat circulating system primarily circulating heat in arthropod harbourages or directing heat towards an interface between the enclosure and the cover.

6. The encasement of claim 1, wherein the heating source is disposed on interior surfaces of the enclosure and wherein a further heat source is in direct contact with the furniture element and/or with arthropod harbourage.

7. The encasement of claim 1, wherein the furniture element is configurable between a retracted configuration and an expanded configuration, wherein in the retracted configuration, the furniture element is within the enclosure and wherein in the expanded configuration, the furniture element expands at least partially outside the enclosure.

8. The encasement of claim 7, further comprising an arthropod trap positioned between the furniture element and the enclosure.

9. The encasement of claim 8, wherein the encasement further comprises at least one leg for supporting the encasement on a ground surface.

10. The encasement of claim 9, wherein the leg comprises an arthropod trap.

11. The encasement of claim 10, wherein the arthropod trap is a glue trap.

12. The encasement of claim 11, further comprising an isolating structure for isolating the furniture element with respect to the enclosure.

13. The encasement of claim 12, wherein the isolating structure further comprises:
- a first surface having a first end, a second end and a pair of lateral sides extending from the first end to the second end;
- an overhang structure provided along the pair of lateral edges and the second end; and
- a second surface extending upwardly from the first end,
- wherein the first surface, the overhang structure and the second surface are isolated from the enclosure.

14. The encasement of claim 13, wherein the isolating structure further comprises at least one leg supporting the isolating structure.

15. The encasement of claim 14, wherein the at least one leg comprises an arthropod trap.

16. The encasement of claim 15, wherein the arthropod trap is a glue trap.

17. The encasement of claim 16, wherein the isolating structure is a bed frame, wherein the second surface is a headboard and wherein the bed frame and the second surface are offset from the enclosure.

18. The encasement of claim 17, further comprising an object to be decontaminated.

19. The encasement of claim 18, wherein the object is selected from the group consisting of: pillows, blankets, sheets, duvets, bags, carpets, linen, clothing, curtains, electronic devices and books.

* * * * *